(12) United States Patent
Bertolotti et al.

(10) Patent No.: US 7,932,422 B2
(45) Date of Patent: Apr. 26, 2011

(54) USE OF CHLORINE GUANABENZ DERIVATIVES FOR TREATING POLYGLUTAMINE EXPANSION ASSOCIATED DISEASES

(76) Inventors: Anne Bertolotti, Cambridge (GB); Marc Blondel, Saint Pol de Léon (FR)

( * ) Notice: Subject to any disclaimer, the term of this patent is extended or adjusted under 35 U.S.C. 154(b) by 0 days.

(21) Appl. No.: 12/311,433

(22) PCT Filed: Oct. 3, 2007

(86) PCT No.: PCT/IB2007/004177
§ 371 (c)(1),
(2), (4) Date: Mar. 30, 2009

(87) PCT Pub. No.: WO2008/041133
PCT Pub. Date: Apr. 10, 2008

(65) Prior Publication Data
US 2010/0036166 A1 Feb. 11, 2010

(30) Foreign Application Priority Data
Oct. 4, 2006 (EP) .................................. 06291547

(51) Int. Cl.
*C07C 281/16* (2006.01)
(52) U.S. Cl. ........ 564/227; 564/226; 564/228; 564/237; 564/249; 564/251
(58) Field of Classification Search .............. None
See application file for complete search history.

(56) References Cited

U.S. PATENT DOCUMENTS
2005/0148673 A1 7/2005 Harbut et al.

FOREIGN PATENT DOCUMENTS
WO 94/27591 12/1994

OTHER PUBLICATIONS

The Merck Index, 14th Edition ver. 14.4 (on-line edition copyright 2006, 2009), Merck & Co. Inc., Whitehouse Station, New Jersey, entry: Guanabenz.*
International Search Report for PCT/IB2007/004177, mailed Jul. 29, 2008.
Farber et al., "Alpha-2 Adrenergic Agonists Prevent MK-801 Neurotoxicity", Neuropsychopharmacology, vol. 12, No. 4, 1995, pp. 347-349, XP002411329.
Martel et al., "Neuroprotective Effects of the Alpha2-adrenoceptor Antagonists, (+)-efaroxan and (Racemic)-idazoxan, Against Quinolinic Acid-Induced Lesions of the Rat Straiatum", Experimental Neurology, vol. 154, No. 2, Dec. 1998, pp. 595-601, XP002411330.

* cited by examiner

*Primary Examiner* — Brian J Davis
(74) *Attorney, Agent, or Firm* — Nixon & Vanderhye, P.C.

(57) ABSTRACT

The invention relates to chlorine Guanabenz derivatives for treating Huntington's disease and other polyglutamine expansion associated diseases. More specifically, it relates to the use of the molecule of formula (I) wherein R=H or Cl and the phenyl group is at least substituted twice, or a pharmaceutically acceptable salt thereof, for the manufacture of a medicament for treating polyglutamine expansion associated diseases.

5 Claims, 3 Drawing Sheets

USE OF CHLORINE GUANABENZ DERIVATIVES FOR TREATING POLYGLUTAMINE EXPANSION ASSOCIATED DISEASES

This application is the U.S. national phase of International Application No. PCT/IB2007/004177, filed 3 Oct. 2007 which designated the U.S. and claims priority to European Application No. 06291547.5, filed 4 Oct. 2006, the entire contents of each of which are hereby incorporated by reference.

The invention relates to chlorine Guanabenz derivatives for treating Huntington's disease and other polyglutamine expansion associated diseases.

Huntington's disease (HD) is caused by a faulty gene on chromosome 4. This gene, discovered in 1993, produces a protein called Huntingtin and leads to a damage of the nerve cells in areas of the brain. The degeneration of the nerve cells causes gradual physical, mental and emotional changes.

The early symptoms of HD are slight, uncontrollable muscular movements, stumbling and clumsiness, lack of concentration, short-term memory lapses, depression and changes of mood, sometimes associated with aggressive or antisocial behaviour.

Later on in the illness, some other symptoms may also appear such as involuntary movements, difficulty in speech and swallowing, weight loss. Emotional changes result in stubbornness, frustration, mood swings and often, depression, and cognitive changes mainly concern a loss of initiative and organization skills and a difficulty in concentrating.

At this time, there is no way to stop or to reverse the course of HD. Secondary illnesses, such as pneumonia, are often the actual causes of the death of the patient.

Scientific investigations show that a proteolytic fragment of the huntingtin protein containing expanded polyglutamine (polyQ) forms inclusions in patient brains, transgenic mice and cellular models of Huntington's diseases. The molecular cascade linking aggregate formation and cellular dysfunction remains elusive. While numerous evidences correlate aggregation with cytotoxicity, the precise nature of the neurotoxic entity remains so far elusive. The pathogenic conformer may not reside in the mature insoluble fibrils but rather in a soluble oligomeric precursor. The final product of the aggregation process might even be protective. Yet, oligomerization of expanded polyQ was reported to be crucial for their pathogenicity and interfering with oligomerization revealed beneficial. Considerable efforts have been devoted to develop high-throughput assays to identify compounds of therapeutic interest. Chemical inhibitors of amyloids such as Congo Red have been identified in vitro. However, chemical compounds identified for their potent ability to inhibit polyQ oligomerization in a cell-free assay often turn out to be toxic for cells.

Huntington's disease belongs to a broader group of disorders characterized by expansion of CAG codons translated in glutamine in unrelated proteins. While Huntington's disease is caused by an expansion in the gene encoding Huntingtin, Spinal and bulbar muscular atrophy, Dentalorubral-pallidoluysian atrophy, and Spinocerebellar ataxias 1, 2, 3, 6, 7 and 17 are caused by expansion in genes encoding Androgen Receptor, Atrophin 1, Ataxin 1, 2, 3, α-voltage dependent calcium channel subunit and TBP respectively. CAG expansion is translated in polyglutamine and causes aggregation of the affected protein.

The aim of the invention is then to provide non toxic compounds capable of treating polyglutamine expansion associated diseases.

In a first study, the inventors have screened several chemically diverse libraries of compounds (consisting of either synthetic molecules or natural products purified from various sources by academic laboratories) for the ability to cure aggregated proteins. In a further study, they tested the selected screened compounds in cellular models of HD.

The work of the inventors has allowed them to isolate an active compound, which is an already used medicine crossing the blood-brain barrier.

Thus the present invention concerns the isolation of Guanabenz, a drug already in clinic for the treatment of hypertension, as active against polyglutamine expansion associated diseases.

The results disclosed in the example part demonstrate that the treatment of polyglutamine associated diseases and Huntington's disease in particular, is a new potential therapeutic indication for Guanabenz.

More particularly the present invention relates to the use of the molecule of formula:

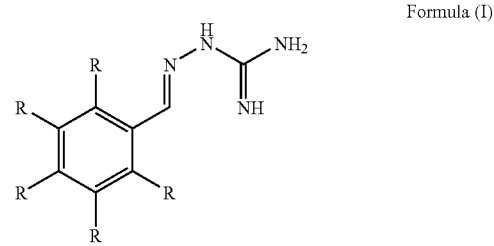

Formula (I)

wherein R=H or Cl and the phenyl group is at least substituted twice, or a pharmaceutically acceptable salt thereof, for the manufacture of a medicament for treating polyglutamine expansion associated diseases.

In a preferred embodiment, the molecule according to the invention is the Guanabenz, or a pharmaceutically acceptable salt thereof, for the manufacture of a medicament for treating polyglutamine expansion associated diseases.

By the term Guanabenz, it is meant a compound of formula:

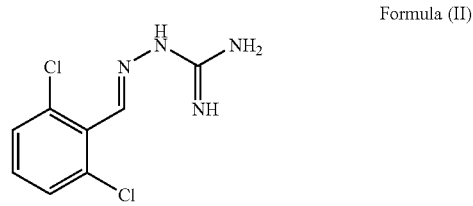

Formula (II)

or a salt thereof, more particularly the acetate salt of formula:

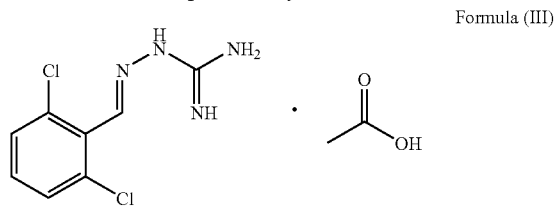

Formula (III)

In another preferred embodiment, the molecule according to the invention has formula:

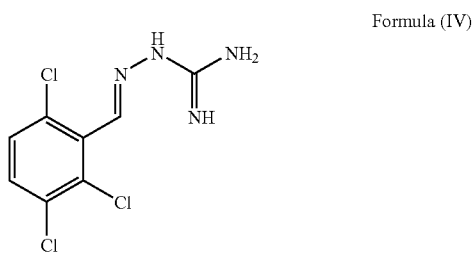

Formula (IV)

or a pharmaceutically acceptable salt thereof, for the manufacture of a medicament for treating said diseases.

The present invention also relates to a method of treatment comprising the administration of a therapeutically effective amount of a compound of formula (I) to (IV) together with a pharmaceutically acceptable carrier to a patient in the need thereof.

By "treatment", it is meant reversing, alleviating, inhibiting the progress of, or preventing the disorder or one or more symptoms of such disorder.

By "therapeutically effective amount", it is intended an amount of a compound of the invention effective in preventing or treating pathological of polyglutamine expansion associated diseases.

The therapeutically effective amount can be determined by the physician or anyone skilled in the art, depending of the size, age and general health of the patient, its specific disease involved and its severity, the mode of administration and other relevant circumstances. A daily dose comprises in the range of 0.01 mg/kg to 0.1 g/kg of body weight is preferred. However, for guanabenz acetate, the preferred daily dose range is from 0.01 mg/kg to 1 mg/kg of body weight, the maximum recommended human daily dose being around 1.3 mg/kg.

The compounds of the invention can be delivered in different formulation, depending of the mode of administration: oral, parenteral, inhalation, topical, intracerebroventricular administration. Preferred mode of administration is oral route.

The characteristics and advantages of the present invention are illustrated by the following examples, with references to FIGS. 1 to 3, which represent:

a: erg6Δ, [PSI$^{30}$] yeast strain, which grows as white colonies, was plated on a Petri dish containing appropriate medium and small filters such as the ones used in antibiograms were placed on the agar surface. Individual compounds were applied on each filter as described in Bach et al, 2003. When a compound is active, a halo of red [psi$^-$] colonies appears around the filter were it was spotted. In the example shown, 2 compounds Psi114, and Cl-Psi114 are active. GuHCL, guanidine hydrochloride, serves as a positive control b: 293T cells were transfected with Htt48 and treated with the indicated compounds in DMSO at the indicated doses or DMSO alone 4 h posttransfection. SDS lysates collected 48 h post-transfection were analyzed on a 10% SDS-PAGE followed by immunoblot with Htt 2B4 and vimentin antibodies. To reveal full length Huntingtin, the same extracts were analyzed on a 4.5% SDS-PAGE followed by immunoblot PAGE followed by immunoblot with an oligoclonal mixture of Huntingtin antibodies: 2B4, 4C8 and 2E8.

c: Filter retardation assay of the same lysates revealed by immunoblot with huntingtin 2B4 antibody.

Figure 2:
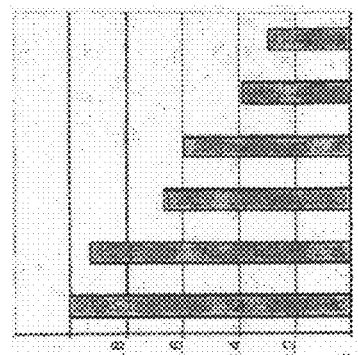
Figure 2:
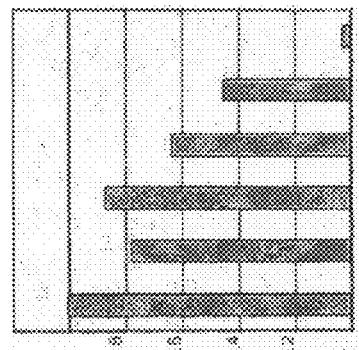
Figure 2:
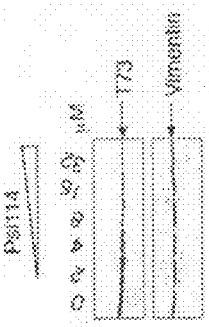
Figure 2:
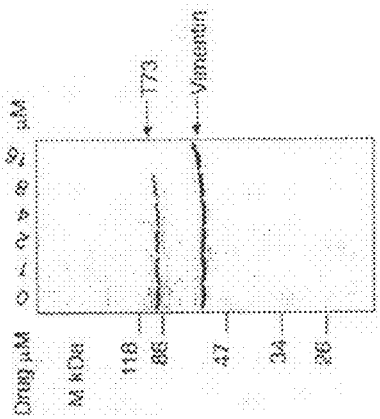

FIG. 2: Activity of Guanabenz (Psi114) and Chloroguanabenz (Cl-Psi114) compounds in neuronal like cell model of HD.

NG108-15 cells were induced for differentiation and T73 expression as described in Lunkes et al, 2002 and treated with the indicated compounds in DMSO at the indicated doses or DMSO alone 12 h post-induction. SDS lysates collected 48 h post-transfection were analyzed by SDS-PAGE followed by immunoblot with Htt 2B4 and vimentin antibodies. Images were acquired and quantified with the Chemi-Smart system (Vilber Lourmat). Quantification of T73 signals is presented as histograms. Signal from DMSO treated cells is used as a reference and set as 1.

Figure 3:
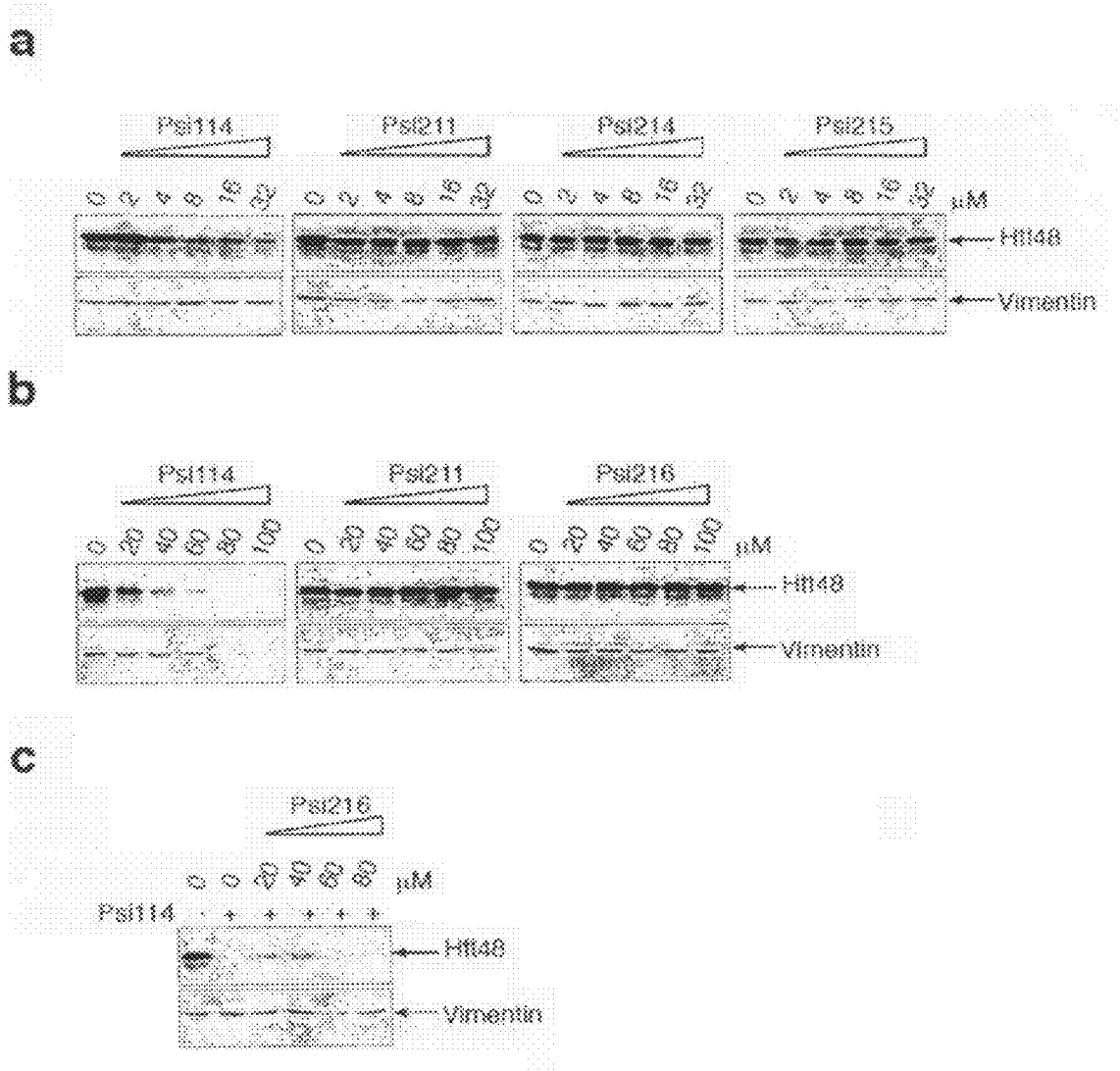

FIG. 3: Activity of compounds binding to the α-2 adrenergic receptor, the known target of Psi114.

a,b: 293T cells were transfected with Htt48 and treated with the indicated compounds in DMSO at the indicated doses or DMSO alone 4 h post-transfection. SDS lysates collected 48 h post-transfection were analyzed on a 10% SDS-PAGE followed by immunoblot with Htt 2B4 and vimentin antibodies.

c: Same as in a, b except that cells where treated with either DMSO alone (lane 1), 40 μM Psi114 (lanes 2-6) together with Psi216 (Efaroxan) at the indicated doses.

EXAMPLE 1

Activity of Guanabenz and Chloroguanabenz in a Transiently Transfected Cellular Model of HD (293T Cells)

a. Results

Figure 1:
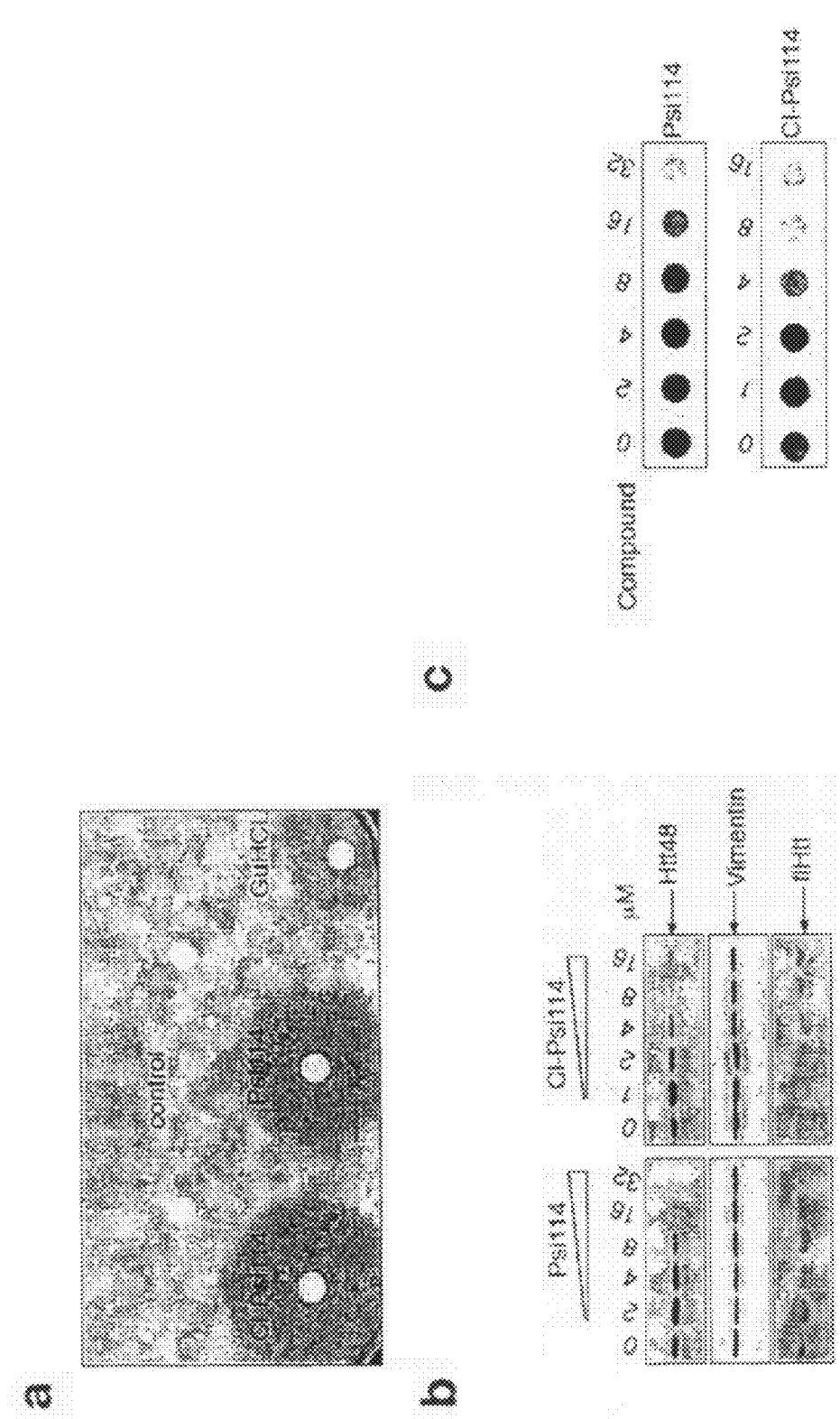
FIG. 1: Activity of Guanabenz (Psi114) and Chloroguanabenz (Cl-Psi114) in yeast and in a transiently transfected cell model of Huntington's disease.

A yeast-based calorimetric high-throughput method has been developed to isolate potent inhibitors of aggregated proteins (yeast prion based test, patent application EP 1551992). About 15000 molecules have been screened from various libraries amongst which, Guanabenz (called Psi114 in this study), an already used medicine used for treatment of an unrelated disease, which has been selected for further study due to its potent activity against yeast prions. Chloroguanabenz (Cl-Psi114) was obtained by medicinal chemistry and revealed more active in the yeast anti-prion screen that Psi114 (FIG. 1a). GuHCL, a well characterized inhibitor of yeast prions is shown as a control. The inventors tested the most active inhibitors of yeast prions, Psi114 and Cl-Psi114 in a transiently transfected cellular model of HD. 293T cells were transfected with a construct expressing a N-terminal fragment of Huntingtin derivative with 48 glutamines and treated with the indicated doses of compounds. This model is a very stringent one to test the activity of chemical compounds because the expression level and aggregation propensity of the overexpressed polyQ derivative are very high. In this stringent system, Congo red has a barely detectable activity at a dose of 500 μM. SDS extracts were performed 48 h post-transfection and analyzed both by immunoblots and filter retardation assay. Measurement of the cellular protein vimentin was used as a toxicity assessment since cellular protein concentration varies with cell density. While the levels of vimentin remain largely constant over a treatment ranging form 0 to 32 μM or 16 μM of Psi114 or Cl-Psi114 respectively, the levels of both soluble Htt48 and aggregated Htt48 decrease in a dose dependent manner upon treatment with both compounds (FIGS. 1 b and c). Notably, the decrease provoked by Psi114 on soluble Htt48 is already visible at 8 μM (FIG. 1b) while its effect on aggregated material (FIG. 1c) is delayed suggesting that Psi114 targets an early event in Htt48 accumulation. The compounds Psi114 and Cl-Psi114 efficiently reduce accumulation of a pathogenic fragment of Huntingtin in a transiently transfected cellular model of HD.

b. Discussion

Psi114 and Cl-Psi114 reduce polyQ accumulation both in their soluble and insoluble form. In developing therapeutic approaches, targeting specifically the pathogenic fragment of Huntingtin is a fundamental concern because Huntingtin is an essential gene. The inventors tested the effect of active compounds on endogenous full length Huntingtin in the same extracts as tested for the N-terminal fragment of Huntingtin.

Psi114 and Cl-Psi114 have no effect on the levels of full length endogenous Huntingtin in 293T cells while these 2 compounds effectively reduce accumulation of the N-terminal pathogenic fragment of Huntingtin (FIG. 1b). Cl-Psi114 has also no effect on the level of full length endogenous Huntingtin in HD patient lymphoblastoid cell line. Together, these data indicate that the compounds Psi114 and Cl-Psi114 specifically reduce accumulation of the disease linked N-terminal fragment of Huntingtin protein.

EXAMPLE 2

Activity of Guanabenz and Chloroguanabenz in a Neuronal-Like Cell Model of HD (NG108-15 Cells)

The Guanabenz (Psi114) and Chloroguanabenz (Cl-Psi114) effects were so far tested in actively dividing yeast and 293T cells (Lunkes et al., 1998). Because neurons are the target of Huntington and the threat for accumulation of misfolded proteins being exacerbated in neuronal, post-mitotic cells, the inventors next tested the effect of Psi114 and Cl-Psi114 in NG10815 neuronal-like cell model of HD. NG108-15 cells were induced for expression of truncated huntingtin with 73Q repeats (T73) and differentiation.

Drugs were added 12 h post-induction at the indicated doses. Protein extracts were collected 3 days after treatment and analyzed by immunoblots. Psi114 and Cl-Psi114 provoke a reduction of T73 in a dose dependant manner while vimentin level remains unaltered (FIG. 2 a-c). The aggregates formed in these cells were below the detection level of the filter retardation assay precluding a robust quantitative analysis of the effects of the molecules on aggregate. However, because both aggregates and pathological symptoms are reversible with blockade of pathological protein expression, it is likely that aggregates in NG108-15 cells will diminish as a consequence of decreased accumulation of T73 by treating neurons with Psi114 or Cl-Psi114.

Guanabenz (Psi114) is a marketed compound that has been patented several decades ago. The molecular target of Psi114 is well known and numerous derivatives have been obtained that display agonistic or antagonistic activities over α-2-adrenergic receptor. Importantly, one antagonist of α-2-adrenergic receptor, Efaroxan (Psi216), has been subjected to clinical tests in HD. Therefore, the inventors decided to investigate whether the observed activity of Psi114 as a potential drug against HD was a general property of compounds binding to Psi114 target or a specific property of Psi114. As a first hint in answering this question, it was noted that Psi114 is active in yeast cells, said yeast cells lacking the known target of Psi114. This suggests that the potential prion curing activity of Psi114, and presumably its activity towards accumulation of the pathogenic fragment of Huntingtin, involves a different target and thus a different mechanism than the currently known mechanism of action of this drug. Nevertheless, the inventors tested a few known agonists or antagonists of the receptor of Psi114. Treatment with Clonidine (Psi211), Cirazoline (Psi214) and Rilmenidine (Psi215) are without any detectable effects at doses where Psi114 reduces accumulation of the soluble pathogenic fragment of Huntingtin (FIG. 3 a). While Psi215 and Psi214 exhibit some toxicity at higher doses, Psi211 and Psi216 are still completely inactive in the inventors assay up to 100 μM (FIG. 3b). Additionally, Psi216 was tested to determine whether it could antagonize the effect of Psi114 in reducing accumulation of expanded polyQ and the inventors found that addition of 80 μM of Psi216 does not alter the efficiency by which Psi114 reduces accumulation of the soluble Htt48. Together, these results have major implications. The activity of Psi114 is not a general activity of molecules binding to the known target of Psi114. Moreover, the mechanism by which Psi114 reduces accumulation of expended polyQ probably involves a distinct target as the known Psi114 target. Based on these criteria, the activity proposed for Psi114 as a cure for HD is a novel activity which could not have been anticipated based on prior work on compounds binding to the same molecular target. The inventors therefore conclude that Guanabenz may have different targets.

EXAMPLE 3

Therapeutic Composition Comprising Guanabenz, for Treating Huntington's Disease

Composition of a tablet suitable for oral administration:
Guanabenz acetate
Lactose
Dicalcium phosphate
Corn starch
Colloidal silica
Povidone
Stearic acid
Soluble starch
Posology
4 mg of guanabenz acetate, twice a day.

REFERENCES

Bach, S. et al. Isolation of drugs active against mammalian prions using a yeast-based screening assay. *Nat Biotechnol* 21, 1075-81. Epub 2003 Aug. 10. (2003)

Lunkes, A. & Mandel, J. L. A cellular model that recapitulates major pathogenic steps of Huntington's disease. *Hum Mol Genet* 7, 1355-61. (1998)

Lunkes, A. et al. Proteases acting on mutant huntingtin generate cleaved products that differentially built up cytoplasmic and nulear inclusions. *Mol Cell* 10, 259-69. (2002)

The invention claimed is:
1. A method of alleviating the symptoms of a polyglutamine expansion associated disease comprising administering to a person in need of said alleviating a molecule of the following formula (I):

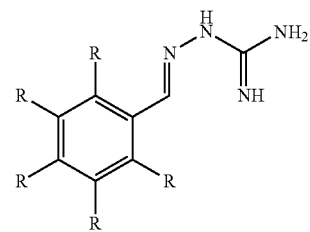

wherein R is H or Cl and the phenyl group is at least substituted twice, or a pharmaceutically acceptable salt thereof.

2. The method of claim 1, wherein the molecule is of the following formula (II):

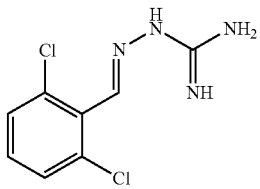

or a pharmaceutically acceptable salt thereof.

3. The method of claim 2, wherein the molecule is the acetate salt of the following formula (III):

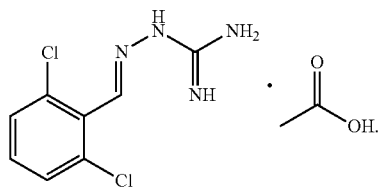

4. The method of claim 1, wherein the molecule is of the following formula (IV):

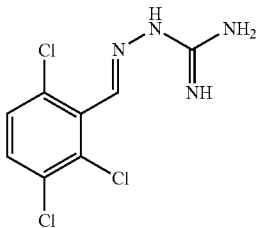

or a pharmaceutically acceptable salt thereof.

5. The method of claim 1, wherein the polyglutamine expansion associated disease is selected from the group consisting of Huntington's disease, Kennedy disease, amyotrophic lateral sclerosis, cerebellous autosomic ataxies, dentalorubral pallidoluysian atrophy of spino-bulbar amyotrophy.

* * * * *